United States Patent [19]

Lang et al.

[11] 4,118,501

[45] Oct. 3, 1978

[54] THIAZOLIDINE DERIVATIVES

[75] Inventors: Hans-Jochen Lang, Altenhain, Taunus; Roman Muschaweck, Frankfurt am Main, both of Fed. Rep. of Germany

[73] Assignee: Hoechst Aktiengesellschaft, Frankfurt am Main, Fed. Rep. of Germany

[21] Appl. No.: 759,546

[22] Filed: Jan. 14, 1977

[30] Foreign Application Priority Data

Jan. 17, 1976 [DE] Fed. Rep. of Germany ....... 2601598

[51] Int. Cl.$^2$ ................ A61K 31/425; C07D 277/14; C07D 277/18

[52] U.S. Cl. ................. 424/270; 260/293.68; 544/96; 544/111; 544/242; 544/278; 544/369

[58] Field of Search ................. 260/306.7 T; 424/270

[56] References Cited

U.S. PATENT DOCUMENTS

| 3,652,577 | 3/1972 | Manning | 260/306.7 T |
|---|---|---|---|
| 3,660,418 | 5/1972 | Manning | 260/306.7 T |
| 3,704,240 | 11/1972 | Wei et al. | 260/306.7 T |

*Primary Examiner*—Donald G. Daus
*Assistant Examiner*—James H. Turnipseed
*Attorney, Agent, or Firm*—Curtis, Morris & Safford

[57] ABSTRACT

4-(Sulfamoyl-phenyl)-4-hydroxy-2-imino-thiazolidine-derivatives having salidiuretic activity and a process for their manufacture.

11 Claims, No Drawings

THIAZOLIDINE DERIVATIVES

The present invention relates to thiazolidine derivatives and to a process for preparing them.

The present invention provides thiazolidine derivatives of the general formula I

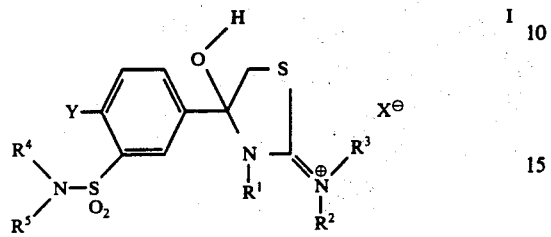

and/or the tertiary bases thereof which correspond to the formula Ia

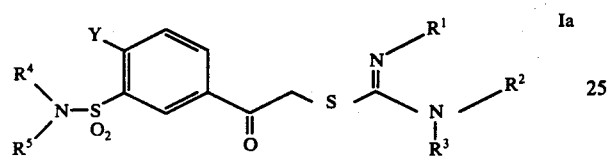

in which $R^1$ represents alkyl or alkenyl radicals of 1 to 4 carbon atoms or cycloalkyl radicals of 3 to 6 carbon radicals, $R^2$ and $R^3$ are identical or different and represent alkyl radicals of 1 to 6 carbon atoms, cycloalkyl radicals of 3 to 6 carbon atoms, alkenyl radicals of 3 to 4 carbon atoms, phenylalkyl radicals of 1 to 3 carbon atoms in the alkyl moiety, or a phenyl radical, and in which $R^1$ and $R^2$ may together also represent an alkylene chain of 2 or 3 carbon atoms and/or $R^2$ together with $R^3$ may stand for an alkylene chain of 4 to 7 carbon atoms which may be branched and wherein a methylene group may be replaced by an O-atom or a $NCH_3$-group, wherein Y represents hydrogen, bromine or chlorine, $R^4$ stands for hydrogen or an alkyl radical of 1 to 4 carbon atoms, $R^5$ is hydrogen, an alkyl radical of 1 to 4 carbon atoms, cycloalkyl of 5 to 7 carbon atoms, benzyl, the aromatic nucleus of which may be substituted by chlorine or methyl, or phenylethyl, and in which $R^4$ together with $R^5$ may also represent an alkylene chain of 4 to 7 carbon atoms which may be branched, and X represents the anion of a pharmacologically tolerated acid.

The invention furthermore relates to a process for preparing the compounds of the general formula I, which comprises reacting (a) compounds of the general formula II

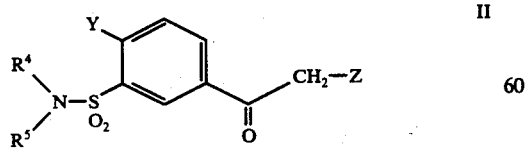

in which $R^4$, $R^5$ and Y are defined as above and Z stands for the radical of an activated ester of an inorganic or organic acid, with thio-ureas of the general formula III, which may be present in the two formulae IIIa and IIIb

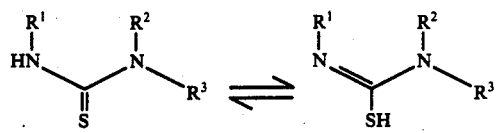

in which $R^1$, $R^2$ and $R^3$ are defined as above, or (b) reacting compounds of the general formula IV

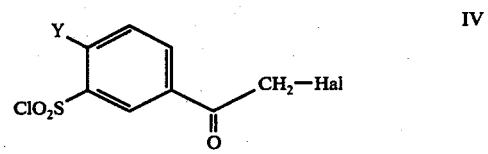

in which Y is defined as above and Hal stands for Cl cr Br, with thio-ureas of the formula III and reacting the thiazolidine derivatives of the general formula V obtained

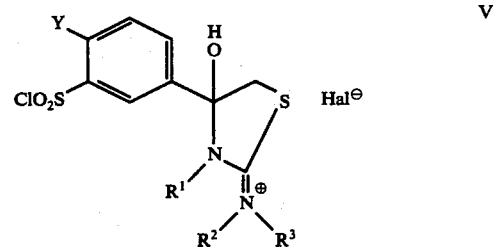

in which $R^1$, $R^2$ and $R^3$ are defined as above, with ammonia, a primary or secondary amine of the general formula VI

in which $R^4$ and $R^5$ are defined as above, or (c) reacting compounds of the general formula VII

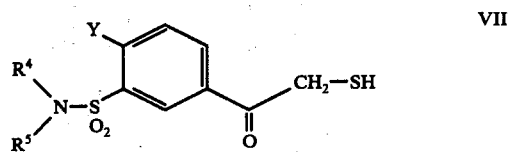

with compounds of the formula VIII

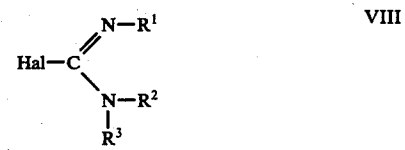

with $R^1$ through $R^5$ and Y being defined as above and Hal standing for chlorine or bromine, or (d) treating compounds of the general formula IX

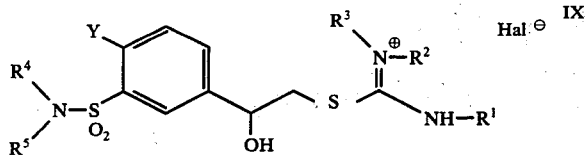

in which $R^1$ through $R^5$ and Y are defined as above and Hal stands for chlorine or bromine, with an oxidizing agent,
and, if desired, converting the salts of the general formula I (X = anion of an acid) obtained according to methods (a) through (d) with organic or inorganic bases into their corresponding basic compounds Ia or transforming bases of the formula Ia obtained with acids HX into the salts of the formula I.

Inorganic acids which may be used are, for example, hydrohalic acids such as hydrochloric acid and hydrobromic acid, as well as sulfuric acid, phosphoric acid and amido-sulfonic acid.

Organic acids which may be used are, for example, formic acid, acetic acid, benzoic acid, succinic acid, fumaric acid, maleic acid, lactic acid, tartaric acid, citric acid, salicylic acid, oxyethanesulfonic acid, ethylenediaminetetraacetic acid, methane-sulfonic acid, p-toluenesulfonic acid, etc.

The quaternary compounds I may also be present in their tautomeric form Ib:

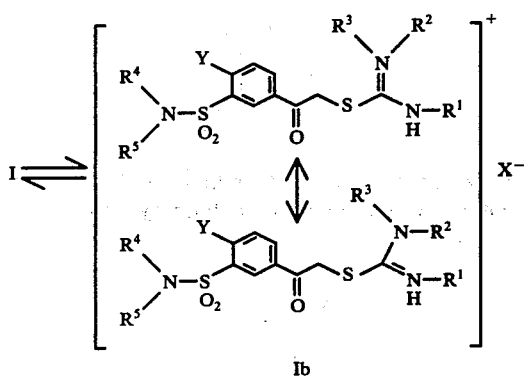

The compounds of the formula I of the invention may, in addition, also be present in their possible geometrical isomeric structures.

The alkyl and/or alkenyl radicals in the substituents $R^1$ to $R^5$ may be straight-chained as well as branched.

The corresponding tertiary basic compounds which may be obtained and derived from compounds I and/or Ib are exclusively present in the non-cyclic form Ia.

In the quaternary compounds of the general formula I of the invention, only the cyclic form has been indicated in the following as one of the possible isomeric and/or tautomeric forms of a respective substance.

Method (a) is carried out advantageously by reacting the compounds of the formula II with the thio-ureas of the formula III in a molar ratio of 1:1 to 1:1.5. Higher molar excess amounts of thio-urea generally do not give significant advantages. The reaction is advantageously carried out in an inert solvent, for example in polar organic solvents such as dimethyl-formamide, dimethylacetamide, dioxane, tetrahydrofurane, acetonitrile, nitromethane, diethylene-glycol-dimethyl ether, etc.

As particularly advantageous reaction mediums proved acetic acid lower alkyl esters such as methyl acetate and ethyl acetate, lower alcohols containing 1 to 4 carbon atoms, in particular methanol, ethanol, isopropanol, and lower dialkyl ketones, for example acetone and methyl-ethyl ketone. Mixtures of the mentioned solvents may also be used as well as mixtures of the mentioned solvents with less appropriate solvents, for example methanol/benzene, ethanol/toluene, methanol/diethyl ether, ethanol/carbon tetrachloride, acetone/chloroform, it being of advantage that the solvent with a higher polarity be present in an excess amount. The reaction partners may be present in the respective solvent in suspended or dissolved form. On principle, the reaction partners may also be reacted without using a solvent, in particular in those cases where the respective thio-urea has a very low melting point, but in these cases side-reactions may occasionally occur due to the exothermic reaction course. The reaction proceeds moderately exothermically and can be carried out at between 0° and 100° C., preferably at between 10° and 70° C. Particularly advantageous proved a temperature range of from 20° to 55° C.

The reaction time depends largely on the reaction temperature and is between 2 minutes in the higher temperature ranges and 60 hours at lower temperatures. In the favourable temperature range, the reaction time is generally between 5 minutes and 40 hours.

In many cases the compounds I are separated in the course of the reaction in a sparingly soluble form, in which case the yield may be increased by optionally adding an appropriate precipitant subsequently at the end of the reaction. As precipitants there may be used, for example, hydrocarbons, such as benzene, toluene, cyclohexane, petroleum ether, ligroine, carbon tetrachloride; there are suitable, in particular, acetic acid-lower alkyl esters containing 1 to 4 carbon atoms in the alkyl moiety, such as ethyl acetate and n-butyl-acetate, dialkylethers having 4 to 8 carbon atoms, such as diethyl ether, diisopropyl ether and di-n-butyl ether. If, after termination of the reaction, a solution is obtained, the salts of the formula I are precipitated with one of the afore-mentioned precipitants, optionally after previous concentration of the reaction solution, or, advantageously, in order to remove inhomogeneous impurities, the solution is filtered into one of the mentioned precipitants, while stirring. Since the reaction of the compounds II with the thio-ureas III, if effected under optimum conditions, practically proceeds quantitatively, the crude products so obtained of the desired compounds are in most cases already analytically pure.

The thio-ureas III used have for the most part been described in literature. They are obtained, for example, by the reaction of amines with isothio-cyanates or thiophosgene (cf. Houben-Weyl, "Methoden der organischen Chemie", vol. 9, p. 884, 4th edition, 1955).

In the compounds of the formula II, there may be used as the radical of an activated ester Z, for example, Cl, Br, J, $CH_3$—$SO_2$—O—, $C_2H_5$—$SO_2$—O—, $C_6H_5$—$SO_2$—O—, $CH_3C_6H_4$—$SO_2$—O—. They may be obtained according to several methods.

In this way, the diazo-ketones of the general formula XI

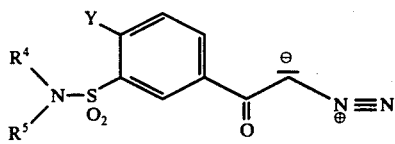

may be converted with acids into the ketones of the formula II. This process as well as a number of compounds II and XI are known in literature (Swiss Pat. No. 389,591 and Belgian Pat. No. 610,633); the other compounds of formula II may be prepared and reacted accordingly.

Since diazoalkanes are extremely poisonous, explosive and difficult to manipulate, the compounds of the formula II, in which $R^4$, $R^5$ and Y have the meanings given above and Z represents chlorine or bromine, are prepared in a more advantageous manner by reacting compounds of the general formula XII

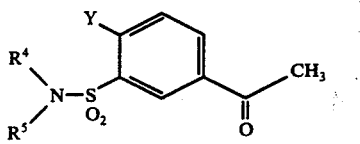

with a suitable halogenating agent, for example with elementary chlorine or bromine, sulfuryl chloride, mono-chloro-urea, copper-II bromide, bromodioxane, N-bromosuccinimide under conditions known from literature.

The compounds XII which are easily accessible are known in the case where Y stands for chlorine, with $R^4 = R^5$ representing hydrogen (Arzneimittel-Forsch. 13, 269 (1963)); the other compounds of formula XII required for the process of the invention are prepared in an analogous manner.

Finally, the compounds of the formula II may also be obtained by reacting under conditions known from literature the α-hydroxy-ketones known from Swiss Pat. No. 389,591 of the general formula XIII,

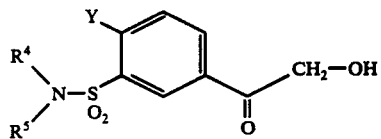

or compounds which have been substituted accordingly and which may be prepared in an analogous manner, with the activated derivatives of organic and inorganic acids, such as methane-sulfonic acid chloride, ethane-sulfonic acid chloride, benzene-sulfonic acid chloride, p-toluene-sulfonic acid chloride, thionyl bromide, phosphorus trichloride, phosphorus tribromide, phosphorus oxide chloride.

The hydroxy-ketones required with $R^4$ = H, $R^5$ standing for hydrogen or lower alkyl, Y representing hydrogen and halogen, are known (Swiss Pat. No. 389,591).

According to the process variant specified under (b), sulfochlorides of the general formula IV are reacted with thio-ureas III in a reaction medium using solvents as described under process variant (a) with exception of alcohols however. The molar ratios of the reactants, the temperature ranges and reaction periods correspond likewise to the specifications given in process variant (a).

The thiazolidines obtained of the formula V separate in most cases during the reaction in a sparingly soluble form and, optionally after previous concentration, the yield of V can be increased by the addition of a suitable precipitant.

As precipitants, the solvents used in method (a) for the same purpose are suitable. If, after termination of the reaction, a solution is obtained, the compounds of the formula V are precipitated, optionally after previous concentration of the reaction mixture, with one of the above-mentioned precipitants or the reaction mixture is advantageously filtered into the respective solvent, while stirring. The compounds of the formula V are in most cases very pure. In any case, should a purification of the compounds V be necessary, they can be recrystallized from an inert solvent which is free from water and alcohol as far as possible, for example acetone, methylethyl ketone, acetonitrile, nitro-methane. The method of dissolution and reprecipitation is particularly advantageous, since it avoids a strong thermal strain of compounds V. For this purpose the respective raw product of the formula V is dissolved in a pure and inert solvent, for example dimethylformamide, dimethyl-acetamide, acetone, acetonitrile, nitromethane, at a temperature in the range of from 0° to 30° C., the solution is optionally treated with charcoal and after filtration the compounds are precipitated with one of the above-mentioned precipitants.

The clearness of the reaction course in the reaction of the halogeno-ketones IV with the thio-ureas III to give the thiazolidines V is insofar surprising as, on the other hand, the thio-ureas III react specifically with the bromo-ketone radical in IV, without attacking the chloro-sulfonyl group, and, on the other hand, that the sulfochloride function in the compounds IV and V does not react with the hydroxy function of the compounds V despite the presence of the thio-ureas III which react as weak bases.

The sulfonic acid chlorides of the general formula V so obtained are then reacted with ammonia or with an amine of the formula VI to give compounds of the formula Ia. Aqueous solutions of ammonia and of the amines VI as well as liquid ammonia or pure amines may be used in excess amounts, the excess ammonia or amine serving at the same time as solvent. The reaction may also be carried out in organic solvents, for example dimethylformamide, dimethylacetamide, dimethyl-sulfoxide, dioxane, tetrahydrofurane, diethyleneglycol-dimethyl ether, the lower alcohols of 1 to 4 carbon atoms, for example methanol, ethanol or isopropanol, being especially suitable. For the reaction of the sulfochlorides V into the corresponding sulfonamides, 1 mole of ammonia or amine VI in the presence of 2 moles of an auxiliary base are theoretically necessary. Per mole of sulfochloride V, at least 3 moles of ammonia or amine VI are used, but it may be advantageous to use a larger excess of about 3 to 7 moles of ammonia or amine VI per one mole of sulfochloride, or more. It is also possible to operate with 1 or 2 moles of ammonia or amine VI, if the operation is carried out in the presence of an auxiliary base, using about 1 to 6 molar equivalents of auxiliary base. As auxiliary bases, inorganic and organic hydroxides, carbonates and bi-carbonates, as well as salt solutions of weak inorganic or organic acids, the tertiary amines such as triethylamine, tri-n-butyl-amine, methyl-dicyclohexylamine, ethyl-dicyclohexylamine being particularly advantageous in all cases. The tertiary amine may likewise serve, if used in an excess amount, as reaction medium without addition of another solvent. The reaction proceeds exothermically and it is of advantage to work at temperatures in the range of from $-35°$ to $+40°$ C., preferably from $+10°$ to $+25°$ C. The reaction time should be at least 30 minutes and the reaction should be worked up after 5 hours at the latest. The working up is carried out, optionally after removal by distillation of the amine, by diluting the reaction mixture with water whereupon the compounds of formula Ia precipitate in a sparingly soluble form. If $R^4$ or $R^5$ represents a hydrogen atom, the pH-value should be adjusted as far as possible to 7.5 to 8.5. Directly after the precipitation with water, the compounds often separate in the form of viscous oils which crystallize more or less rapidly. The crystallization can be accelerated by several treatments with a suitable solvent, for example water, ether, diisopropyl ether, carbon tetrachloride, petroleum ether, n-butyl-acetate.

After the precipitation with water, the compounds obtained are preferably extracted with an appropriate solvent, preferably with an acetic acid-lower alkyl ester, such as methyl acetate or ethyl acetate. After drying, the extract is concentrated under reduced pressure.

The basic compounds Ia may then be converted without further isolation and purification into the corresponding quaternary acid addition products of the formula I by treatment with a protonic acid.

The halogenoketones IV required for process (b) are obtained from the ketones of the formula XIV

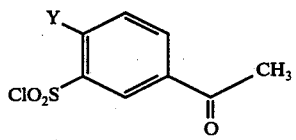

in known manner with suitable halogenation agents, for example those described in process (a) above for the halogenation of compounds XII.

According to method (c), the compounds of the formula VII are reacted in a solvent with the known compounds of the formula VIII. As solvents, lower alcohols having 1 to 4 carbon atoms, as well as lower alkyl esters of acetic acid having 1 to 4 carbon atoms in the alkyl moiety, such as methyl acetate and ethyl acetate, are particularly suitable.

The reactions are generally carried out within a temperature range of from 0° to 60° C., preferably from 15° to 35° C., the reaction time being between 5 and 60 hours. Particularly suitable for this reaction are especially compounds VII which carry at the sulfamoyl group, besides $R^4$ = hydrogen, a voluminous organic radical $R^5$, such as cycloheptyl or tert. butyl, or those compounds VII, in which $R^4$ and $R^5$ each have an organic radical as substituent.

The compounds of the formula VII used in method (c) may be prepared in various ways. For example, the compounds of the formula II can be converted with thiocarboxylic acids of the formula XV

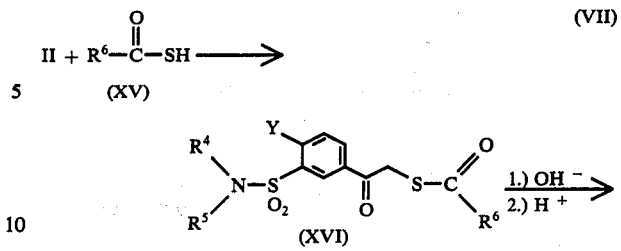

preferably with thioacetic acid ($R^6=CH_3$) in the presence of one equivalent of base, for example KOH, in an aqueous or alcoholic medium, into the thio-esters of the general formula XVI which are hydrolyzed in a slightly alkaline medium to give the compounds of the formula VII.

Another possibility consists in the reaction of the compounds of the formula II with alkali metal hydrogeno-sulfides in an inert solvent such as sodium or potassium bisulfide in dimethylformamide at temperatures between 0° and 40° C. The methods yielding compounds VII are known from literature.

According to method (d), the compounds of the general formula IX are converted with the aid of a suitable oxidizing agent, preferably with active manganese-IV oxide, into the compounds of the formula I or the corresponding bases Ia. As solvents, preferably halogenated hydrocarbons such as methylene chloride, chloroform, tetrachloroethane are used, and the reaction is carried out at temperatures in the range of from 0° to 40° C., preferably from 20° to 30° C., over a period of time of 10 to 60 hours.

The starting compounds of the formula IX are obtained by converting the halogenoketones of the formula II, in which Z preferably represents chlorine or bromine, for example according to the method described in Arzneimittelforschung 22, 2095 (1972) with a suitable reducing agent, preferably with sodium boron hydride in methanol at temperatures between 0° and 25° C. into compounds of the formula XVII

XVII $$\underset{R^5}{\overset{R^4}{\diagdown}}N-\underset{O_2}{S}-\overset{Y}{\underset{}{\diagup\!\!\!\!\diagdown}}-\underset{\underset{H}{\overset{}{|}}}{\overset{H}{\underset{}{|}}}\underset{O}{\overset{}{C}}-CH_2-Z$$

As alkyl-halides, the compounds of the formula XVII react with the thio-ureas of the formula III to give the iso-thio-uronium salts of the formula IX. The reaction conditions correspond to those indicated for method (a).

The compounds of the formula Ia can be reacted in reversible manner in a suitable solvent with an acid of the formula H—X. The basic compounds Ia can be introduced into the pure acids at temperatures in the range of from 0° to 40° C., provided that these acids are liquid or have a melting point which is not essentially higher than 40° C. It is, however, advantageous to work in a solvent, for example in water, or in an organic solvent, for example in dioxan, tetrahydrofuran, ether, an acetic acid-lower alkyl ester containing 1 to 4 carbon atoms in the alkyl moiety, acetonitrile, nitromethane, acetone, methyl-ethyl ketone, etc., lower alcohols containing 1 to 4 carbon atoms having proved to be especially suitable. Per mole of the basic compounds Ia, 1 to 1.5 moles of the acids H—X are used, it being also possible to use higher amounts of acid. It is suitable to operate at temperatures between 0° and 40° C., preferably between 10° and 25° C. The reaction is moderately exothermic.

When working in an aqueous solution, the acid addition compounds are only rarely separated directly after the addition of acids H—X. If this is not the case, the salts are isolated by a careful evaporation of the water, preferably by lyophilization. When working in organic solvents, the acid addition salts I are often separated in a sparingly soluble form after the addition of the acid. Said compounds are otherwise precipitated by means of a precipitant, optionally after previous concentration. As precipitants, there are suitable the precipitants described for the same purpose under method (a).

Even when they show a very high degree of purity, compounds I are very often obtained in the form of viscous oils or amorphous glass-like products. These products can be brought to crystallization in many cases by treating them with an organic solvent, optionally while heating between 40° to 80° C. There are suitable for this purpose, in particular, lower alkyl acetates having 1 to 4 carbon atoms in the alkyl moiety, such as methyl acetate, ethyl acetate, n-butyl acetate as well as lower dialkyl ketones, such as acetone or methylethylketone, lower dialkyl ethers, such as diethyl ether, diisopropyl ether or di-n-butyl ether, as well as acetonitrile, nitromethane, and in some cases also lower alcohols, such as methanol, ethanol, isopropanol or n-butanol.

The quaternary compounds I may be deprotonized in an appropriate solvent by a treatment with bases, to give the tertiary compounds of the general formula Ia. As bases there may be used, for example, solutions of inorganic hydroxides, such as lithium, sodium, potassium, calcium, or barium hydroxides, carbonates or bicarbonates, such as sodium carbonate, potassium carbonate, sodium or potassium bicarbonate, ammonia and amines, for example, triethylamine, dicyclohexylamine, piperidine, methyl-dicyclo-hexylamine.

When working in an aqueous medium, the basic compounds of the formula Ia precipitate in a sparingly soluble form and can be separated and isolated by filtration or extraction with an organic solvent, preferably with ethyl acetate. Suitable organic reaction mediums are in particular lower alcohols containing 1 to 4 carbon atoms, preferably methanol and ethanol, but ethyl acetate, diethyl ether, tetrahydrofuran, dioxan, diethylene glycol-dimethyl ether or dimethylformamide may also be used.

The most important compounds of the invention are those corresponding to the general formula I, in which the substituent $R^1$ is methyl, ethyl or allyl, $R^2$ and $R^3$ are ethyl, 1-propyl, 2-propyl, 1-butyl-, 2-butyl, $R^4$ and $R^5$ are hydrogen, X and Y represent chlorine or bromine.

Furthermore, there may be mentioned as preferred compounds those of the formula I, in which $R^1$, X and Y are defined as above and in which $R^3$ represents a benzyl or phenylethyl radical, if $R^2$ stands for methyl or ethyl, $R^2$ is connected with $R^3$ via a pentamethylene chain which may be branched by 1 or 2 methyl groups, the medium methylene group possibly being replaced by an O-atom or a N—$CH_3$ group, $R^5$ represents methyl, benzyl and phenylethyl, and $R^4$ stands for hydrogen or methyl.

In addition to the 4-(3-sulfamoyl-phenyl)-1,3-thiazolidine-4-ols described in the Examples, there may also be obtained, according to the invention, for example the compounds of the general formula I

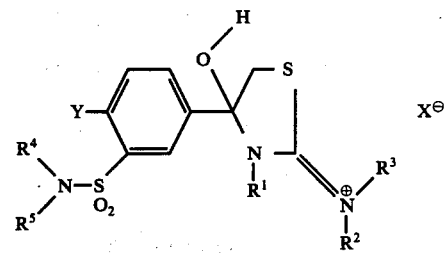

which have been listed in the following Tables.

TABLE I

| | $R^1$ | $R^2$ | $R^3$ | $R^4$ | $R^5$ | Y | X |
|---|---|---|---|---|---|---|---|
| 1 | $CH_3$ | $C_2H_5$ | $C_2H_5$ | H | H | Br | Cl |
| 2 | $CH_3$ | $C_2H_5$ | $C_2H_5$ | H | $n-C_4H_9$ | Cl | Cl |
| 3 | $C_2H_5$ | $C_2H_5$ | $C_2H_5$ | H | $H_5C_6-CH_2$ | Cl | Br |
| 4 | $C_2H_5$ | $C_2H_5$ | $C_2H_5$ | H | $n-C_4H_9$ | Cl | Br |
| 5 | $C_2H_5$ | $C_2H_5$ | $C_2H_5$ | $n-C_3H_7$ | $n-C_3H_7$ | Cl | Br |
| 6 | $C_2H_5$ | $CH_3$ | $n-C_3H_7$ | H | H | Cl | Cl |
| 7 | $CH_3$ | $CH_3$ | $n-C_3H_7$ | H | H | Cl | Cl |
| 8 | $C_2H_5$ | $C_2H_5$ | $n-C_3H_7$ | H | H | Cl | Cl |
| 9 | $C_2H_5$ | $C_2H_5$ | $n-C_4H_9$ | H | H | Cl | Cl |
| 10 | | $-(CH_2)_2-$ | $CH_3$ | H | H | Cl | Cl |
| 11 | | $-(CH_2)_2-$ | $C_2H_5$ | H | H | Cl | Cl |
| 12 | | $-(CH_2)_2-$ | $CH_3$ | $CH_3$ | $CH_3$ | Cl | Br |
| 13 | | $-(CH_2)_2-$ | $C_2H_5$ | H | H | Cl | Cl |
| 14 | $C_2H_5$ | $CH_3$ | $sec-C_4H_9$ | H | H | Cl | Cl |
| 15 | $CH_3$ | $CH_3$ | $CH_2=CH$<br>    $\|$<br>    $CH_2$ | H | H | Cl | Cl |
| 16 | $CH_3$ | $CH_3$ | $CH_2=CH$<br>    $\|$<br>    $CH_2$ | $CH_3$ | $CH_3$ | Cl | Br |
| 17 | $CH_3$ | $C_2H_5$ | $CH_2=CH$<br>    $\|$<br>    $CH_2$ | H | H | Cl | Cl |
| 18 | $C_2H_5$ | $CH_3$ | $CH_2=CH$<br>    $\|$<br>    $CH_2$ | H | H | Cl | Cl |
| 19 | $C_2H_5$ | $C_2H_5$ | $CH_2=CH$<br>    $\|$<br>    $CH_2$ | H | H | Cl | Cl |

TABLE I-continued

| | R¹ | R² | R³ | R⁴ | R⁵ | Y | X |
|---|---|---|---|---|---|---|---|
| 20 | CH₃ | CH₃ | CH₃–CH=CH–CH₂– | H | H | Cl | Cl |
| 21 | CH₃ | C₂H₅ | C₆H₅–CH₂–CH₂– | H | H | Cl | Cl |
| 22 | C₂H₅ | C₂H₅ | C₆H₅–CH₂–CH₂– | H | H | Cl | Cl |
| 23 | CH₃ | CH₃ | C₆H₅–CH(CH₃)– | H | H | Cl | Cl |
| 24 | CH₃ | C₂H₅ | C₆H₅–CH(CH₃)– | H | H | Cl | Cl |
| 25 | C₂H₅ | C₂H₅ | C₆H₅–CH(CH₃)– | H | H | Cl | Cl |
| 26 | CH₃ | C₂H₅ | OH–CH₃ (cyclohexyl) | H | H | Cl | Cl |
| 27 | CH₃ | CH₃ | cyclopentyl | H | H | Cl | Cl |
| 28 | C₂H₅ | C₂H₅ | cyclopentyl | H | H | Cl | Cl |
| 29 | CH₃ | C₂H₅ | cyclopentyl | H | H | Cl | Cl |
| 30 | C₂H₅ | n-C₄H₉ | cyclopentyl | H | H | Cl | Cl |
| 31 | C₂H₅ | –(CH₂)₅– | | H | H | Cl | Cl |
| 32 | C₂H₅ | –(CH₂)₂–O–(CH₂)₂– | | H | H | Cl | Cl |
| 33 | C₂H₅ | –(CH₂)₂–N(CH₃)–(CH₂)₂– | | H | H | Cl | Cl |
| 34 | C₂H₅ | –CH(CH₃)–(CH₂)₃– | | H | H | Cl | Cl |
| 35 | CH₃ | –CH(CH₃)–(CH₂)₃– | | H | H | Cl | Cl |
| 36 | CH₂=CH–CH₂ | –(CH₂)₅– | | H | H | Cl | Cl |
| 37 | CH₂=CH–CH₂ | –(CH₂)₂–O–(CH₂)₂– | | H | H | Cl | Cl |
| 38 | CH₂=CH–CH₂ | –(CH₂)₂–N(CH₃)–(CH₂)₂– | | H | H | Cl | Cl |
| 39 | C₂H₅ | C₂H₅ | C₂H₅ | H | H | H | Cl |
| 40 | C₂H₅ | C₂H₅ | C₂H₅ | H | H | H | Br |
| 41 | CH₃ | C₂H₅ | C₂H₅ | H | H | H | Br |
| 42 | C₂H₅ | CH₂=CH–CH₂ | CH₂=CH–CH₂ | H | H | H | Br |
| 43 | CH₃ | CH₃ | CH₂–C₆H₅ | H | H | H | Br |
| 44 | CH₃ | –(CH₂)₅– | | H | H | H | Br |
| 45 | C₂H₅ | C₂H₅ | C₂H₅ | H | CH₂–C₆H₅ | H | Br |
| 46 | C₂H₅ | C₂H₅ | C₂H₅ | CH₃ | CH₃ | H | Br |
| 47 | C₂H₅ | CH₃ | CH₂–C₆H₅ | CH₃ | CH₃ | H | Br |
| 48 | CH₃ | n-C₄H₉ | n-C₄H₉ | CH₃ | CH₃ | H | Br |

The compounds of the invention are valuable medicaments and are distinguished by a very good diuretic and saluretic action.

The salidiuretic action of the novel compounds of the invention was determined on the rat with a unit dose of 50 mg/kg per os. It was found that this action was superior to the salidiuretic action of known commercial preparations of this thiazide group, for example the hydrochlorothiazide, and to that of chlorothalidone. In addition thereto, the novel compounds of the invention are distinguished by a long lasting action period.

Therefore, the novel compounds of the invention are suitable in particular for the treatment of hypertonic conditions in humans, in which case they will be combined optionally with an antihypertonic agent, as it is usual today.

Therapeutic compositions of the novel compounds are in particular tablets, dragees, capsules, suppositories as well as ampouls for parenteral administration (i.v., s.c. and i.m.). The therapeutical dosage unit is between 5 and 500 mg, preferably from 10 to 100 mg, per tablet.

In addition to the usual filler and carrier substances, these compositions may also contain an antihypertensive agent, especially if they are intended for the therapy of high blood pressure, for example reserpin, hydralazine, guanethidine, α-methyldopa or clonidine.

Moreover, therapeutical combination compositions with potassium-retaining compounds such as aldosterone-antagonists, for example spironolactone, or pseudoaldosterone-antagonists such as Triamterene or Amiloride are of interest. Furthermore, the K+-substitution may also be made with the aid of various forms of administration, for example dragees, tablets, effervescent tablets, lotions, etc.

The following Examples illustrate the invention. In these examples, the melting and decomposition points are not corrected. If a compound is obtained in an amorphous form, its softening and decomposition points are generally considerably lower than in the corresponding crystalline form.

EXAMPLE 1

3-Ethyl-4-(4-chloro-3-sulfamoyl-phenyl)-2-N,N-dimethyliminio-1,3-thiazolidine-4-ol-bromide 3.13 Grams (0.01 mole) of 2-bromo-4'-chloro-3'-sulfamoylaceto-phenone are dissolved in 40 ml of acetone and 1.32 g (0.01 mole) of 1-ethyl-3-dimethyl-thio-urea are added. The mixture is heated to 40° C. within 20 minutes, while stirring with a magnetic stirrer, then the stirring is continued over night at room temperature, and the crystalline precipitate is filtered off.

Colorless crystals, melting point 215° C. (decomposition).

EXAMPLE 2

3-Ethyl-4-(4-chloro-3-sulfamoyl-phenyl)-2-N,N-diethyliminio-1,3-thiazolidine-4-ol-bromide is obtained according to Example 1 from 2-bromo-4'-chloro-3'-sulfamoyl-acetophenone and 1,3,3-triethyl-thio-urea.

Colorless crystals, melting point 182° C. (decomposition).

EXAMPLE 3

4-(4-Chloro-3-sulfamoyl-phenyl)-3-methyl-2-N,N-dimethyliminio-1,3-thiazolidine-4-ol-bromide is obtained according to Example 1 from 2-bromo-4'-chloro-3'-sulfamoyl-acetophenone with 1,3,3-trimethyl-thio-urea. The solvent is decanted off from the oily-amorphous precipitate, and the product is brought to crystallization under diisopropylether.

Colorless crystals, melting point 187° C. (decomposition).

EXAMPLE 4

4-(4-Chloro-3-di-n-propylsulfamoyl-phenyl)-3-methyl-2-N,N-dimethyliminio-1,3-thiazolidine-4-ol-bromide is obtained according to Example 1 from 2-bromo-4'-chloro-3'-di-n-propylsulfamoyl-acetophenone with 1,3,3-trimethyl-thiourea, by subsequently pouring the reaction mixture into 100 ml of diisopropylether being stirred by means of a magnetic stirrer, and by filtering the crystalline precipitate.

Colorless crystals, melting point 174° C. (decomposition).

EXAMPLE 5

4-(4-Chloro-3-sulfamoyl-phenyl)-3-methyl-2-N,N-tetramethyleneiminio-1,3-thiazolidine-4-ol-bromide is obtained according to Example 3 from 2-bromo-4'-chloro-3'-sulfamoyl-acetophenone and 1-methyl-3,3-tetramethylene-thiourea.

Colorless crystals, melting point 175° C. (decomposition).

EXAMPLE 6

3-Allyl-4-(4-chloro-3-dimethylsulfamoyl-phenyl)-2-N,N-diethyliminio-1,3-thiazolidine-4-ol-bromide is obtained according to Example 1 from 2-bromo-4'-chloro-3'-dimethylsulfamoyl-acetophenone and 1-allyl-3,3-diethyl-thiourea. The clear reaction solution obtained is then introduced into 100 ml of stirred ethyl acetate, in which process the desired product precipitates.

Colorless crystals, melting point 130° C. (decomposition).

EXAMPLE 7

3-Ethyl-4-(3-benzylsulfamoyl-4-chloro-phenyl)-2-N,N-dimethyliminio-1,3-thiazolidine-4-ol-bromide is obtained according to Example 1 from 3'-benzylsulfamoyl-2-bromo-4'-chloro-acetophenone and 1-ethyl-3,3-dimethyl-thiourea. The solvent is decanted off from the oily-amorphous precipitate, the latter is treated with 50 ml of diethylether, and the solid matter obtained is filtered off.

Colorless crystals, melting point 139° C. (decomposition).

EXAMPLE 8

3-Allyl-2-N-benzyl-N-methyliminio-4-(4-chloro-3-dimethylsulfamoyl-phenyl)-1,3-thiazolidine-4-ol-bromide is obtained according to Example 7 from 2-bromo-4'-chloro-3'-dimethylsulfamoyl-acetophenone and 1-allyl-3-benzyl-3-methylthioa-urea.

Colorless amorphous solid matter, decomposition starting at 61° C.

EXAMPLE 9

4-(4-Chloro-3-dimethylsulfamoyl-phenyl)-3-cyclohexyl-2-N,N-diethyliminio-1,3-thiazolidine-4-ol-bromide 3.41 Grams of 2-bromo-4'-chloro-3'-dimethylsulfamoyl-acetophenone are dissolved in 50 ml of ethyl acetate, and 2.14 g of 1-cyclohexyl-3,3-diethyl-thio-urea are added. The mixture is stirred for about 15 hours at room temperature, and the crystals are filtered off, melting point 150° C. (decomposition).

EXAMPLE 10

3-Ethyl-4-[4-chloro-3-N,N-tetramethylene-sulfamoyl-phenyl]-2-N,N-diethyliminio-1,3-thiazolidine-4-ol-bromide is obtained according to Example 1 from 2-bromo-4'-chloro-3'-N,N-tetramethylene-sulfamoyl-acetophenone and 1,3,3-triethylthio-urea, the reaction mixture is introduced with filtration into diethylether, is then allowed to stand over night, and the solid matter is filtered off.

Amorphous solid matter, decomposition starting at 140° C.

EXAMPLE 11

4-(4-Chloro-3-dimethylsulfamoyl-phenyl)-2-N,N-diethyliminio-3-isopropyl-1,3-thiazolidine-4-ol-bromide is obtained according to Example 1 by reacting 2-bromo-4'-chloro-3'-dimethylsulfamoyl-acetophenone with 1,1-diethyl-3-isopropylthio-urea and subsequently adding 200 ml of diisopropylether. The solvent is decanted off from the oily precipitate, and the amorphous residue is brought to crystallization under diethylether.

Colorless crystals, melting point 156° C. (decomposition).

EXAMPLE 12

4-(4-Chloro-3-methylsulfamoyl-phenyl)-2-N,N-diethyliminio-3-methyl-1,3-thiazolidine-4-ol-bromide is obtained according to Example 11 by reacting 2-bromo-4'-chloro-3'-methylsulfamoyl-acetophenone with 1,1-diethyl-3-methyl-thio-urea in acetone and precipitating the product with diisopropyl ether. The residue is dissolved in 100 ml of water and is lyophilized.

Colorless amorphous solid matter, decomposition starting at 155° C.

EXAMPLE 13

3-Ethyl-4-(4-chloro-3-methylsulfamoyl-phenyl)-2-N,N-diethyliminio-1,3-thiazolidine-4-ol-bromide is obtained according to Example 12 from 2-bromo-4'-chloro-3'-methylsulfamoyl-acetophenone with 1,3,3-triethyl-thio-urea.

Colorless amorphous hygroscopic solid matter, decomposition starting at 115° C.

EXAMPLE 14

3-Ethyl-4-[4-chloro-3-(2-phenylethyl-sulfamoyl)-phenyl]-2-N,N-diethyliminio-1,3-thiazolidine-4-ol-bromide is obtained according to Example 1 from 2-bromo-4'-chloro-3'-(β-phenylethyl-sulfamoyl)-acetophenone and 1,3,3-triethyl-thiourea in acetone. By adding 100 ml of ether, an oily-amorphous precipitate is obtained which is brought to crystallization under a small amount of acetone.

Colorless crystals, melting point 147° C. (decomposition).

EXAMPLE 15

2-N-ethyl-N-butyliminio-4-(4-chloro-3-sulfamoyl-phenyl)-3-methyl-1,3-thiazolidine-4-ol-bromide is obtained according to Example 1 from 2-bromo-4'-chloro-3'-sulfamoyl-acetophenone with 1-ethyl-1-n-butyl-3-methyl-thio-urea and by subsequent precipitation with 20 ml of diethylether introduced into the stirred reaction mixture.

Colorless crystals, melting point 174° C. (decomposition).

EXAMPLE 16

3-Allyl-4-(4-chloro-3-sulfamoyl-phenyl)-2-N,N-dibenzyliminio-1,3-thiazolidine-4-ol-bromide is obtained according to Example 11 from 2-bromo-4'-chloro-3'-sulfamoyl-acetophenone and 1-allyl-3,3-dibenzyl-thio-urea. Colorless amorphous solid matter, decomposition starting at 75° C.

EXAMPLE 17

4-(4-Chloro-3-sulfamoyl-phenyl)-3-methyl-2-N-(2-methoxy-phenyl)-N-methyliminio-1,3-thiazolidine-4-ol-bromide is obtained according to Example 11 from 2-bromo-4'-chloro-3'-sulfamoyl-acetophenone and 3-(2-methoxy-phenyl)-1,3-dimethylthio-urea.

Colorless amorphous solid matter, decomposition starting at 96° C.

EXAMPLE 18

4-(4-Chloro-3-dimethylsulfamoyl-phenyl)-2-N,N-diethyliminio-3-methyl-1,3-thiazolidine-4-ol-bromide is obtained according to Example 1 from 2-bromo-4'-chloro-3'-dimethylsulfamoyl-acetophenone and 3,3-diethyl-1-methyl-thiourea.

Colorless crystals, melting point 154° to 156° C. (decomposition).

EXAMPLE 19

3-(4-Chloro-3-dimethylsulfamoyl-phenyl)-3-hydroxy-8-methyl-2,3,6,7-tetrahydro-5H-thiazolo[3,2-a]pyrimidine-8-onium-bromide is obtained according to Example 1 from 2-bromo-4'-chloro-3'-dimethylsulfamoyl-acetophenone and 3-methyl-3,4,5,6-tetrahydro-2-pyrimidine-thiol.

Colorless crystals, melting point 158° C. (decomposition).

EXAMPLE 20

4-(4-Chloro-3-dimethylsulfamoyl-phenyl)-2-N,N-diisopropyl-iminio-3-methyl-1,3-thiazolidine-4-ol-bromide is obtained according to Example 1 from 1,1-diisopropyl-3-methylthio-urea and 2-bromo-4'-chloro-3'-dimethylsulfamoyl-acetophenone.

Colorless crystals, melting point 166° C. (decomposition).

EXAMPLE 21

3-n-Butyl-4-(4-chloro-3-sulfamoyl-phenyl)-2-N,N-dimethyliminio-1,3-thiazolidine-4-ol-bromide is obtained according to Example 1 from 2-bromo-4'-chloro-3'-sulfamoyl-acetophenone and 3,3-dimethyl-1-n-butyl-thio-urea.

Colorless crystals, melting point 177° C. (decomposition).

EXAMPLE 22

2-N,N-di-n-butyliminio-4-(4-chloro-3-sulfamoyl-phenyl)-3-methyl-1,3-thiazolidine-4-ol-bromide is obtained according to Example 1 from 2-bromo-4'-chloro-3'-sulfamoyl-acetophenone and 3,3-di-n-butyl-1-methyl-thio-urea.

Colorless crystals, melting point 196° C. (decomposition).

EXAMPLE 23

3-(4-Chloro-3-sulfamoyl-phenyl)-3-hydroxy-8-methyl-2,3,6,7-tetrahydro-5H-thiazolo[3,2-a]pyrimidine-8-onium-bromide is obtained according to Example 1 from 2-bromo-4'-chloro-3'-sulfamoyl-acetophenone and 2-methyl-3,4,5,6-tetrahydro-2-pyrimidine-thiol.

Colorless crystals, melting point 159° C. (decomposition).

EXAMPLE 24

3-(4-Chloro-3-methylsulfamoyl-phenyl)-3-hydroxy-8-methyl-2,3,6,7-tetrahydro-5H-thiazolo[3,2-a]pyrimidine-8-onium-bromide is obtained according to Example 1 from 2-bromo-4'-chloro-3'-methylsulfamoyl-acetophenone and 3-methyl-3,4,5,6-tetrahydro-2-pyrimidine-thiol.

Colorless crystals, melting point 188° C. (decomposition).

EXAMPLE 25

4-(4-Chloro-3-sulfamoyl-phenyl)-3-methyl-2-[N-methyl-N-(1-methyl-2-hydroxy-2-phenyl-ethyl)-iminio]-1,3-thiazolidine-4-ol-bromide is obtained according to Example 1 by reacting 2-bromo-4'-chloro-3'-sulfamoyl-acetophenone with 1,3-dimethyl-3-(2-hydroxy-2-phenyl-1-methyl-ethyl)-thio-urea.

Colorless amorphous dyestuff. Decomposition starting at 87° C.

EXAMPLE 26

4-(4-Chloro-3-sec.-butylsulfamoyl-phenyl)-3-methyl-2-N,N-dimethyliminio-1,3-thiazolidine-4-ol-bromide is obtained according to Example 1 from 2-bromo-3'-sec.-butyl-4'-chloro-acetophenone and 1,3,3-trimethyl-thio-urea.

Melting point 151° C. (decomposition).

EXAMPLE 27

3-Ethyl-4-(4-chloro-3-sulfamoyl-phenyl)-2-N,N-tetramethyleneiminio-1,3-thiazolidine-4-ol-bromide is obtained according to Example 1 from 1-ethyl-3-tetramethylenethio-urea and 2-bromo-4'-chloro-3'-sulfamoyl-acetophenone.

Melting point 186° C. (decomposition).

EXAMPLE 28

3-Allyl-4-(4-chloro-3-sulfamoyl-phenyl)-2-N,N-tetramethyleneiminio-1,3-thiazolidine-4-ol-bromide is obtained according to Example 1 from 1-allyl-3-tetramethylenethio-urea and 2-bromo-4'-chloro-3'-sulfamoyl-acetophenone.

Melting point 154° C. (decomposition).

EXAMPLE 29

4-(4-Chloro-3-sulfamoyl-phenyl)-2-N-cyclohexyl-N-methyl-iminio-3-methyl-1,3-thiazolidine-4-ol-bromide is obtained according to Example 1 from 1,3-dimethyl-3-cyclohexyl-thio-urea and 2-bromo-4'-chloro-3'-sulfamoyl-acetophenone.

Melting point 196° C. (decomposition).

EXAMPLE 30

4-(4-Chloro-3-sulfamoyl-phenyl)-2-N,N-dibenzyl-iminio-3-methyl-1,3-thiazolidine-4-ol-bromide is obtained according to Example 1 from 3,3-dibenzyl-1-methylthio-urea and 2-bromo-4'-chloro-3'-sulfamoyl-acetophenone.

Melting point 222° C. (decomposition).

EXAMPLE 31

2-N-Butyl-N-piperonyl-iminio-4-(4-chloro-3-sulfamoyl-phenyl)-3-methyl-1,3-thiazolidine-4-ol-bromide is obtained according to Example 1 from methyl-3-n-butyl-3-piperonyl-thio-urea and 2-bromo-4'-chloro-3'-sulfamoyl-acetophenone.

Melting point 139° C. (decomposition).

EXAMPLE 32

3-Ethyl-4-(4-chloro-3-sulfamoyl-phenyl)-2-N,N-diallyl-iminio-1,3-thiazolidine-4-ol-bromide is obtained according to Example 1 from 1-ethyl-3,3-diallylthio-urea and 2-bromo-4'-chloro-3'-sulfamoyl-acetophenone.

Melting point 154° C. (decomposition).

EXAMPLE 33

4-(4-Chloro-3-methylsulfamoyl-phenyl)-3-methyl-2-N,N-(3-oxapentamethylene-iminio)-1,3-thiazolidine-4-ol-bromide is obtained according to Example 6 from 2-bromo-4'-chloro-3'-methylsulfamoyl-acetophenone and 1-methyl-3,3-(3-oxapentamethylene)-thio-urea).

Colorless crystals, melting point 186° C. (decomposition).

EXAMPLE 34

4-[4-Chloro-3-(2-chlorobenzylsulfamoyl)-phenyl]-3-methyl-2-N,N-(3-methylazapentamethylene-iminio)-1,3-thiazolidine-4-ol-bromide is obtained according to Example 10 from 2-bromo-4'-chloro-3'-(2-chlorobenzylsulfamoyl)-acetophenone and 1-methyl-3,3-(3-methylazapentamethylene)-thio-urea.

Amorphous solid matter, decomposition starting at 85° C.

EXAMPLE 35

4-(3-n-Butylsulfamoyl-4-chloro-phenyl)-2-N,N-dimethyliminio-3-methyl-1,3-thiazolidine-4-ol-bromide is obtained according to Example 4 from 2-bromo-3'-n-butylsulfamoyl-4'-chloro-acetophenone and 1,3,3-trimethyl-thio-urea.

Amorphous solid matter, decomposition starting at 104° C.

EXAMPLE 36

4-(4-Chloro-3-methylsulfamoyl-phenyl)-3-methyl-2-N,N-di-n-propyliminio-1,3-thiazolidine-4-ol-bromide is obtained according to Example 4 from 1-methyl-3,3-di-n-propylthio-urea and 2-bromo-4'-chloro-3'-methylsulfamoyl-acetophenone.

Amorphous solid matter, decomposition starting at 85° C.

EXAMPLE 37

4-(4-Chloro-3-hexahydrobenzylsulfamoyl-phenyl)-3-methyl-2-N,N-diethyliminio-1,3-thiazolidine-4-ol-bromide is obtained according to Example 4 from 2-bromo-4'-chloro-3'-hexahydrobenzylsulfamoyl-acetophenone and 3,3-diethyl-1-methylthio-urea.

Colorless crystals, melting point 161° C.

EXAMPLE 38

4-(3-Ethylsulfamoyl-4-chloro-phenyl)-2-N,N-diethyliminio-3-methyl-1,3-thiazolidine-4-ol-bromide is obtained according to Example 4 from 3'-ethylsulfamoyl-2-bromo-4'-chloro-acetophenone and 3,3-diethyl-1-methyl-thio-urea.

Colorless crystals, melting point 131° C.

EXAMPLE 39

4-[4-Chloro-3-(4-methylbenzylsulfamoyl)-phenyl]-2-N,N-diethyliminio-3-methyl-1,3-thiazolidine-4-ol-bromide is obtained according to Example 4 from 3,3-diethyl-1-methylthio-urea and 2-bromo-4'-chloro-3'-(4-methyl-benzylsulfamoyl)acetophenone.

Amorphous solid matter, decomposition starting at 82° C.

EXAMPLE 40

4-(3-Benzylsulfamoyl-4-chloro-phenyl)-3-methyl-2-N,N-(3-oxapentamethylene-iminio)-1,3-thiazolidine-4-ol-bromide is obtained by slowly heating 4.03 g (0.01 mole) of 3'-benzylsulfamoyl-2-bromo-4'-chloroacetophenone and 1.76 g (0.011 mole) of 3,3-(3-oxapentamethylene)-1-methyl-thio-urea to 45° C., then stirring the mixture for 10 minutes at this temperature and for 4 hours at room temperature. The solvent is decanted off from the viscous oily precipitate, and the residue is brought to crystallization in a two-phase mixture of water and ether.

Amorphous solid matter, decomposition starting at 120° C.

EXAMPLE 41

2-N-Benzyl-N-isopropyliminio-4-(4-chloro-3-sulfamoyl-phenyl)-3-methyl-1,3-thiazolidine-4-ol-bromide is obtained according to Example 6 from 2-bromo-4'-chloro-3'-sulfamoyl-acetophenone and 3-benzyl-3-isopropyl-1-methyl-thiourea.

Amorphous solid matter, decomposition starting at 93° C.

EXAMPLE 42

4-(4-Chloro-3-sulfamoyl-phenyl)-2-N,N-(2,4-dimethyl-3-oxapentamethylene-iminio)-3-methyl-1,3-thiazolidine-4-ol-bromide is obtained according to Example 6 from 2-bromo-4'-chloro-3'-sulfamoyl-acetophenone and 3,3-(2,4-dimethyl-3-oxa-pentamethylene)-1-methyl-thio-urea.

Colorless crystals, melting point 196° C. (decomposition).

EXAMPLE 43

3-Ethyl-2-N,N-diallyliminio-4-(4-chloro-3-di-n-propyl-sulfamoylphenyl)-1,3-thiazolidine-4-ol-bromide is obtained according to Example 10 from 2-bromo-4'-chloro-3'-di-n-propylsulfamoyl-acetophenone and 1-ethyl-3,3-diallyl-thio-urea.

Amorphous solid matter, decomposition starting at 80° C.

EXAMPLE 44

3-Ethyl-2-N,N-diallyl-4-(4-chloro-3-dimethylsulfamoyl-phenyl)-1,3-thiazolidine-4-ol-bromide is obtained according to the method described in Example 10 from 2-bromo-4'-chloro-3'-dimethylsulfamoyl-acetophenone and 1-ethyl-3,3-diallyl-thio-urea.

Amorphous solid matter, decomposition starting at 96° C.

EXAMPLE 45

3-Ethyl-2-N,N-diallyliminio-4-(4-chloro-3-methylsulfamoyl-phenyl)-1,3-thiazolidine-4-ol-bromide is obtained according to Example 4 from 1-ethyl-3,3-diallyl-thio-urea and 2-bromo-4'-chloro-3'-methylsulfamoyl-acetophenone.

Amorphous solid matter, decomposition starting at 94° C.

EXAMPLE 46

3-Ethyl-2-N,N-diallyliminio-4-(4-bromo-3-sulfamoyl-phenyl)-1,3-thiazolidine-4-ol-bromide is obtained according to Example 4 from 1-ethyl-3,3-diallyl-thiourea and 2,4'-dibromo-3'-sulfamoyl-acetophenone.

Amorphous solid matter, decomposition starting at 90° C.

EXAMPLE 47

2,N,N-Diallyliminio-3-n-butyl-4-(4-chloro-3-sulfamoyl-phenyl)-1,3-thiazolidine-4-ol-bromide is obtained according to Example 4 from 3,3-diallyl-1-n-butyl-thiourea and 2-bromo-4'-chloro-3'-sulfamoyl-acetophenone.

Amorphous solid matter, decomposition starting at 88° C.

EXAMPLE 48

3-Ethyl-2-N-ethyl-N-cyclohexyliminio-4-(4-chloro-3-methylsulfamoyl-phenyl)-1,3-thiazolidine-4-ol-bromide is obtained according to Example 4 from 1,3-diethyl-3-cyclohexylthio-urea and 2-bromo-4'-chloro-3'-methyl-sulfamoyl-acetophenone.

Amorphous solid matter, decomposition starting at 81° C.

EXAMPLE 49

3-Ethyl-2-N,N-dibenzyliminio-4-(4-chloro-3-sulfamoyl-phenyl)-1,3-thiazolidine-4-ol-bromide is obtained according to Example 4 from 1-ethyl-3,3-dibenzylthiourea and 2-bromo-4'-chloro-3'-sulfamoyl-acetophenone.

Amorphous solid matter, decomposition starting at 85° C.

EXAMPLE 50

2-N-Benzyl-N-methyliminio-4-(4-chloro-3-sulfamoyl-phenyl)-3-methyl-1,3-thiazolidine-4-ol-bromide is obtained according to Example 1 from 2-bromo-4'-chloro-3'-sulfamoyl-acetophenone and 3-benzyl-1,3-dimethyl-thio-urea.

Melting point 196° C. (decomposition).

EXAMPLE 51

4-(4-Chloro-3-sulfamoyl-phenyl)-3-methyl-2-N-methyl-N-phenyliminio-1,3-thiazolidine-4-ol-bromide is obtained according to Example 1 from 1,3-dimethyl-3-phenylthio-urea and 2-bromo-4'-chloro-3'-sulfamoyl-acetophenone.

Colorless crystals, melting point 219° C. (decomposition).

EXAMPLE 52

4-(3-Benzylsulfamoyl-4-chloro-phenyl)-3-methyl-2-N,N-tetramethylene-iminio-1,3-thiazolidine-4-ol-bromide is obtained according to Example 1 from 1-methyl-3,3-tetramethylene-thio-urea and 3'-benzylsulfamoyl-2-bromo-4'-chloroacetophenone.

Colorless crystals, melting point 193° C. (decomposition).

EXAMPLE 53

4-(4-Chloro-3-cyclohexylsulfamoyl-phenyl)-3-methyl-2-N,N-dimethyliminio-1,3-thiazolidine-4-ol-bromide is obtained according to Example 1 from 1,3,3-trimethyl-thiourea and 2-bromo-4'-chloro-3'-cyclohexylsulfam-oyl-acetophenone.

Colorless crystals, melting point 178° C. (decomposition).

EXAMPLE 54

4-[4-Chloro-3-(2-phenylethylsulfamoyl)-phenyl]-3-methyl-2-N,N-dimethyliminio-1,3-thiazolidine-4-ol-bromide is obtained according to Example 1 from 1,3,3-trimethyl-thiourea and 2-bromo-4'-chloro-3'-(2-phenylethylsulfamoyl)-acetophenone.

Colorless crystals, melting point 188° C. (decomposition).

EXAMPLE 55

4-(4-Chloro-3-N,N-pentamethylene-sulfamoyl-phenyl)-3-methyl-2-N,N-dimethyliminio-1,3-thiazolidine-4-ol-bromide is obtained according to Example 1 from 1,3,3-trimethyl-thiourea and 2-bromo-4'-chloro-3'-N,N-pentamethylene-sulfamoylacetophenone.

Colorless crystals, melting point 194° C. (decomposition).

EXAMPLE 56

4-(3-N-Benzyl-N-methylsulfamoyl-4-chloro-phenyl)-3-methyl-2-N,N-dimethyliminio-1,3-thiazolidine-4-ol-bromide is obtained according to Example 1 from 1,3,3-trimethyl-thiourea and 3'-N-benzyl-N-methylsulfamoyl-2-bromo-4'-chloroacetophenone.

Colorless crystals, melting point 174° C. (decomposition).

EXAMPLE 57

3-Ethyl-4-(3-ethylsulfamoyl-4-chlorophenyl)-2-N,N-(3-oxapentamethylene-iminio)-1,3-thiazolidine-4-ol-bromide is obtained according to Example 1 from 3'-ethylsulfamoyl-2-bromo-4'-chloro-acetophenone and 1-ethyl-3,3-(3-oxapentamethylene)-thio-urea.

Colorless crystals, melting point 189° C. (decomposition).

EXAMPLE 58

4-(4-Chloro-3-isobutylsulfamoyl-phenyl)-3-methyl-2-N,N-dimethyliminio-1,3-thiazolidine-4-ol-bromide is obtained according to Example 1 from 2-bromo-4'-chloro-3'-isobutyl-sulfamoyl-acetophenone and 1,3,3-trimethyl-thio-urea.

Colorless crystals, melting point 179° C. (decomposition).

EXAMPLE 59

4-(4-Chloro-3-isobutylsulfamoyl-phenyl)-3-methyl-2-N,N-di-n-propyliminio-1,3-thiazolidine-4-ol-bromide is obtained according to Example 1 from 2-bromo-4'-chloro-3'-isobutyl-sulfamoyl-acetophenone and 1-methyl-3,3-di-n-propylthio-urea.

Colorless crystals, melting point 162° C.

EXAMPLE 60

2-N,N-Diethyliminio-4-(4-chloro-3-cyclopentylsulfamoyl-phenyl)-3-methyl-1,3-thiazolidine-4-ol-bromide is obtained according to Example 1 from 2-bromo-4'-chloro-3'-cyclopentylsulfamoyl-acetophenone and 3,3-diethyl-1-methylthio-urea.

Colorless crystals, melting point 158° C. (decomposition).

EXAMPLE 61

4-(4-Chloro-3-cyclopentylsulfamoyl-phenyl)-3-methyl-2-N,N-pentamethylene-iminio-1,3-thiazolidine-4-ol-bromide is obtained according to Example 1 from 2-bromo-4'-chloro-3'-cyclopentylsulfamoyl-acetophenone and 1-methyl-3,3-pentamethylene-thiourea.

Colorless crystals, melting point 172° C.

EXAMPLE 62

2-N,N-Diethyliminio-4-(3-benzylsulfamoyl-4-chlorophenyl)-3-methyl-1,3-thiazolidine-4-ol-bromide is obtained according to Example 1 from 3'-benzylsulfamoyl-2-bromo-4'-chloro-acetophenone and 3,3-diethyl-1-methyl-thio-urea.

Colorless crystals, melting point 144° C.

EXAMPLE 63

4-[4-Chloro-3-(4-methylbenzylsulfamoyl)-phenyl]-3-methyl-2-N,N-(3-oxapentamethylene-iminio)-1,3-thiazolidine-4-ol-bromide is obtained according to Example 1 from 2-bromo-4'-chloro-3'-(4-methylbenzylsulfamoyl)-acetophenone and 1-methyl-3,3-(3-oxapentamethylene)-thio-urea.

Crystals, melting point 169° C. (decomposition).

EXAMPLE 64

2-N-Ethyl-N-phenyliminio-4-(4-chloro-3-sulfamoylphenyl)-3-methyl-thiazolidine-4-ol-bromide is obtained according to Example 1 from 3-ethyl-1-methyl-3-phenylthio-urea and 2-bromo-4'-chloro-3'-sulfamoyl-acetophenone.

Crystals, melting point 205° C.

EXAMPLE 65

3-Ethyl-2-N-butyl-N-phenyliminio-4-(4-chloro-3-sulfamoylphenyl)-1,3-thiazolidine-4-ol-bromide is obtained according to Example 1 from 1-ethyl-3-n-butyl-3-phenyl-thio-urea and 2-bromo-4'-chloro-3'-sulfamoyl-acetophenone.

Amorphous solid matter, decomposition starting at 90° C.

EXAMPLE 66

3-Ethyl-2-N-benzyl-N-methyliminio-4-(4-chloro-3-sulfamoylphenyl)-1,3-thiazolidine-4-ol-bromide is obtained according to Example 1 from 2-bromo-4'-chloro-3'-sulfamoyl-acetophenone and 1-ethyl-3-benzyl-3-methyl-thio-urea.

Colorless crystals, melting point 150° C. (decomposition).

EXAMPLE 67

4-(4-Chloro-3-sulfamoyl-phenyl)-2-N-(2-chlorophenyl)-N-methyliminio-3-methyl-1,3-thiazolidine-4-ol-bromide is obtained according to Example 1 from 2-bromo-4'-chloro-3'-sulfamoyl-acetophenone and 3-(2-chlorophenyl)-1,3-dimethylthio-urea.

Melting point 240° C. (decomposition).

EXAMPLE 68

4-(4-Chloro-3-sulfamoyl-phenyl)-2-N,N-hexamethylene-iminio-3-methyl-1,3-thiazolidine-4-ol-bromide is obtained according to Example 1 from 2-bromo-4'-chloro-3'-sulfamoyl-acetophenone and 3,3-hexamethylene-1-methyl-thiourea.

Colorless crystals, melting point 154° C. (decomposition).

EXAMPLE 69

4-(4-Chloro-3-sulfamoyl-phenyl)-3-methyl-2-N,N-(1-methylpentamethylene-iminio-1,3-thiazolidine-4-ol-bromide is obtained according to Example 1 from 2-bromo-4'-chloro-3'-sulfamoyl-acetophenone and 1-methyl-3,3-(1-methylpentamethylene)thio-urea.

Colorless crystals, melting point 194° C. (decomposition).

EXAMPLE 70

3-Ethyl-2-N-ethyl-N-benzyliminio-4-(4-chloro-3-sulfamoylphenyl)-1,3-thiazolidine-4-ol-bromide is obtained according to Example 1 from 1,3-diethyl-3-benzylthiourea and 2-bromo-4'-chloro-3'-sulfamoyl-acetophenone.

Colorless crystals, melting point 145° C. (decomposition).

EXAMPLE 71

3-Ethyl-2-N,N-diethyliminio-4-(4-bromo-3-sulfamoyl-phenyl)-1,3-thiazolidine-4-ol-bromide is obtained according to Example 1 from 2,4'-dibromo-3'-sulfamoyl-acetophenone and 1,3,3-triethyl-thio-urea.

Colorless crystals, melting point 170° C. (decomposition).

EXAMPLE 72

4-(4-Bromo-3-sulfamoyl-phenyl)-3-methyl-2-N,N-(3-oxapentamethylene-iminio)-1,3-thiazolidine-4-ol-bromide is obtained according to Example 1 from 2,4'-dibromo-3'-sulfamoyl-acetophenone and 1-methyl-3,3-(3-oxapentamethylene)-thiourea.

Colorless amorphous solid matter. Decomposition starting at 107° C.

EXAMPLE 73

3-Ethyl-4-(4-bromo-3-sulfamoyl-phenyl)-2-N,N-tetramethyleneiminio-1,3-thiazolidine-4-ol-bromide is obtained according to Example 1 from 2,4'-dibromo-3'-sulfamoyl-acetophenone and 1-ethyl-3,3-tetramethylene-thio-urea.

Colorless crystals, melting point 191° C. (decomposition).

EXAMPLE 74

3-(4-Bromo-3-sulfamoyl-phenyl)-3-hydroxy-8-methyl-2,3,6,7-tetrahydro-5H-thiazolo[3,2-a]pyrimidine-8-onium-bromide is obtained according to Example 1 from 2,4'-dibromo-3'-sulfamoyl-acetophenone and 3-methyl-3,4,5,6-tetrahydro-2-pyrimidinethiol.

Colorless crystals, melting point 161° C. (decomposition).

EXAMPLE 75

2-N,N-Diallyliminio-4-(4-chloro-3-sulfamoyl-phenyl)-3-cyclohexyl-1,3-thiazolidine-4-ol-bromide is obtained according to Example 1 from 2-bromo-4'-chloro-3'-sulfamoyl-acetophenone and 3,3-diallyl-1-cyclohexyl-thio-urea. Colorless amorphous solid matter, decomposition starting at 90° C.

EXAMPLE 76

4-(4-Chloro-3-sulfamoyl-phenyl)-3-methyl-2-N-(2-phenylethyl)-N-methyliminio-1,3-thiazolidine-4-ol-bromide is obtained according to Example 1 from 1,3-dimethyl-3-(2-phenylethyl)-thio urea and 2-bromo-4'-chloro-3'-sulfamoyl-acetophenone.

Colorless crystals, melting point 181° C. (decomposition).

EXAMPLE 77

3-Ethyl-4-(4-chloro-3-sulfamoyl-phenyl)-2-N-(2-phenylethyl)-N-methyliminio-1,3-thiazolidine-4-ol-bromide is obtained according to Example 1 from 2-bromo-4'-chloro-3'-sulfamoyl-acetophenone and 1-ethyl-3-methyl-3-(2-phenylethyl)thio-urea.

Colorless crystals, melting point 181° C. (decomposition).

EXAMPLE 78

2-N-Allyl-N-cyclohexyliminio-3-ethyl-(4-chloro-3-sulfamoylphenyl)-1,3-thiazolidine-4-ol-bromide is obtained according to Example 1 from 2-bromo-4'-chloro-3'-sulfamoyl-acetophenone and 3-allyl-1-ethyl-3-cyclohexyl-thiourea.

Colorless crystals, melting point 155° C. (decomposition).

EXAMPLE 79

3-Ethyl-4-(4-chloro-3-sulfamoyl-phenyl)-2-N,N-dicyclohexyliminio-1,3-thiazolidine-4-ol-bromide is obtained according to Example 1 from 2-bromo-4'-chloro-3'-sulfamoyl-acetophenone and 1-ethyl-3,3-dicyclohexyl-thio-urea.

Colorless crystals, melting point 158° C. (decomposition).

EXAMPLE 80

3-Ethyl-4-(4-chloro-3-methylsulfamoyl-phenyl)-2-N,N-dicyclohexyliminio-1,3-thiazolidine-4-ol-bromide is obtained according to Example 1 from 2-bromo-4'-chloro-3'-methyl-sulfamoyl-acetophenone and 1-ethyl-3,3-dicyclohexylthio-urea.

Colorless crystals, melting point 160° C. (decomposition).

EXAMPLE 81

3-Ethyl-4-(4-chloro-3-dimethylsulfamoyl-phenyl)-2-N,N-dicyclohexyliminio-1,3-thiazolidine-4-ol-bromide is obtained according to Example 1 from 2-bromo-4'-chloro-3'-dimethyl-sulfamoyl-acetophenone and 1-ethyl-3,3-dicyclohexylthio-urea.

Colorless crystals, melting point 167° C. (decomposition).

EXAMPLE 82

3-Ethyl-2-N-ethyl-N-cyclohexyliminio-4-(4-chloro-3-sulfamoylphenyl)-1,3-thiazolidine-4-ol-bromide is obtained according to Example 1 from 1,3-diethyl-3-cyclohexylthio-urea and 2-bromo-4'-chloro-3'-sulfamoyl-acetophenone.

Melting point 124° C. (decomposition).

EXAMPLE 83

2-N-Ethyl-N-phenyliminio-3-n-butyl-4-(4-chloro-3-sulfamoylphenyl)-1,3-thiazolidine-4-ol-bromide is obtained according to Example 1 from 2-bromo-4'-chloro-3'-sulfamoyl-acetophenone and 3-ethyl-1-n-butyl-3-phenyl-thio-urea.

Melting point 190° C. (decomposition).

EXAMPLE 84

4-(4-Chloro-3-sulfamoyl-phenyl)-3-methyl-2-N,N-(1,5-dimethylpenta-methylene-iminio)-1,3-thiazolidine-4-ol-bromide is obtained according to Example 1 from 2-bromo-4'chloro-3'-sulfamoyl-acetophenone and 1-methyl-3,3-(1,5-dimethyl-pentamethylene)-thio-urea.

Colorless crystals, melting point 160° to 162° C. (decomposition).

EXAMPLE 85

2-N,N-Diethyliminio-4-(4-chloro-3-sulfamoyl-phenyl)-3-methyl-1,3-thiazolidine-4-ol-bromide is obtained according to Example 6 from 2-bromo-4'-chloro-3'-sulfamoyl-acetophenone and 3,3-diethyl-1-methyl-thio-urea.

Colorless crystals, melting point 167° C. (decomposition).

EXAMPLE 86

4-(4-(Chloro-3-sulfamoyl-phenyl)-3-methyl-2-N,N-pentamethyleneiminio-1,3-thiazolidine-4-ol-chloride 2.67 Grams (0.01 mole) of 2,4'-dichloro-3'-sulfamoyl-acetophenone are mixed with 1.60 g (0.01 mole) of 1-methyl-3,3-pentamethylene-thiourea in 30 ml of methanol, and the mixture is stirred for 1 hour at 40° C. and then for 4 hours at 20° C. By the addition of 30 to 50 ml of diisopropylether an amorphous viscous precipitate is obtained which is brought to crystallization under ethyl acetate.

Colorless crystals, melting point 185° C. (decomposition).

EXAMPLE 87

2-N,N-Diethyliminio-4-(4-chloro-3-sulfamoyl-phenyl)-3-methyl-1,3-thiazolidine-4-ol-chloride is obtained according to Example 86 from 2,4'-dichloro-3'-sulfamoyl-acetophenone and 3,3-diethyl-1-methyl-thio-urea.

Colorless crystals, melting point 180° C. (decomposition).

EXAMPLE 88

4-(4-Chloro-3-sulfamoyl-phenyl)-3-methyl-2-N,N-(3-methyl-3-azapentamethylene-iminio)-1,3-thiazolidine-4-ol-chloride is obtained according to Example 86 from 2,4'-dichloro-3'-sulfamoyl-acetophenone and 1-methyl-3,3-(3-methyl-3-azapentamethylene)-thio-urea.

Colorless amorphous solid matter, melting point 85° C. (decomposition).

EXAMPLE 89

4-(4-Chloro-3-sulfamoyl-phenyl)-3-methyl-2-N,N-(3-oxa-pentamethylene-iminio)-1,3-thiazolidine-4-ol-chloride 2,4'-Dichloro-3'-sulfamoyl-acetophenone is reacted according to Example 86 with 1-methyl-3-(3-oxapentamethylene)-thio-urea. The reaction mixture is poured into 40 ml of ethyl acetate, the mixture is stirred, and the crystals are filtered off. Melting point 190° C. (decomposition).

EXAMPLE 90

3-Ethyl-2-N,N-diethyliminio-4-(4-chloro-3-sulfamoyl-phenyl)-1,3-thiazolidine-4-ol-chloride is obtained according to Example 1 from 2,4'-dichloro-3'-sulfamoyl-acetophenone and 1,3,3-triethyl-thio-urea.

Crystals, melting point 171° to 173° C. (decomposition).

EXAMPLE 91

2-N,N-Di-n-butyliminio-4-(4-chloro-3-sulfamoyl-phenyl)-3-methyl-1,3-thiazolidine-4-ol-chloride is obtained according to Example 1 from 2,4'-dichloro-3'-sulfamoyl-acetophenone and 3,3-di-n-butyl-1-methyl-thio-urea.

Colorless crystals, melting point 181° C. (decomposition).

EXAMPLE 92

2-N-Benzyl-N-methyliminio-4-(4-chloro-3-sulfamoyl-phenyl)-3-methyl-1,3-thiazolidine-4-ol-chloride is obtained according to Example 1 from 2,4'-dichloro-3'-sulfamoyl-acetophenone and 3-benzyl-1,3-dimethyl-thio-urea.

Colorless crystals, melting point 140° to 142° C. (decomposition).

EXAMPLE 93

4-(4-Chloro-3-sulfamoyl-phenyl)-3-methyl-2-N,N-(1,5-dimethylpentamethylene-iminio)-1,3-thiazolidine-4-ol-chloride is obtained according to Example 1 from 2,4'-dichloro-3'-sulfamoyl-acetophenone and 1-methyl-3,3-(1,5-dimethyl-pentamethylene)-thio-urea.

Colorless crystals, melting point 178° C. (decomposition).

EXAMPLE 94

4-(4-Chloro-3-sulfamoyl-phenyl)-2-(2,4-dimethyl-3-oxapentamethylene-iminio)-3-methyl-1,3-thiazolidine-4-ol-chloride is obtained according to Example 1 from 2,4'-dichloro-3'-sulfamoyl-acetophenone and 3,3-(2,4-dimethyl-3-oxa-pentamethylene)-1-methyl-thio-urea.

Colorless crystals, melting point 150° C. (decomposition).

EXAMPLE 95

3-Ethyl-2-N,N-diallyliminio-4-(4-chloro-3-sulfamoyl-phenyl)1,3-thiazolidine-4-ol-chloride is obtained according to Example 1 from 2,4'-dichloro-3'-sulfamoyl-acetophenone and 3,3-diallyl-1-ethyl-thio-urea.

Colorless crysstals, melting point 151° C., decomposition starting at 167° C.

EXAMPLE 96

4-(4-Chloro-3-sulfamoyl-phenyl)-3-methyl-2-N,N-tetramethyleneiminio-1,3-thiazolidine-4-ol-chloride is obtained according to Example 1 from 2,4'-dichloro-3'-sulfamoyl-acetophenone and 1-methyl-3,3-tetramethylene-thio-urea.

Colorless crystals, melting point 203° to 205° C. (decomposition).

EXAMPLE 97

4-(4-Chloro-3-dimethylsulfamoyl-phenyl)-3-methyl-2-N,N-dimethyl-iminio-1,3-thiazolidine-4-ol-bromide is obtained according to Example 1 from 2-bromo-4'-chloro-3'-sulfamoyl-acetophenone and 1,3,3-trimethyl-thio-urea.

Colorless crystals, melting point 183° to 185° C.

EXAMPLE 98

4-(4-Chloro-3-dimethylsulfamoyl-phenyl)-3-methyl-2-N,N-dimethyl-iminio-1,3-thiazolidine-4-ol-methylsulfonate (a) 2 Grams of (4'-chloro-3'-dimethylsulfamoyl-acetophenone-2-yl)-methane-sulfonic acid-ester are reacted according to Example 1 with 0.85 g of 1,3,3-trimethyl-thio-urea, the salt is precipitated with diethylether, and the amorphous viscous oil is brought to crystallization under ethyl acetate.

Colorless solid matter, decomposition starting at 124° C. (b) 4.6 Grams of 4-(4-chloro-3-dimethylsulfamoyl-phenyl)-3-methyl-2-N,N-dimethyliminio-1,3-thiazolidine-4-ol-bromide are mixed with 50 ml of water, then 100 ml of ethyl acetate are added to form a layer, and 10 ml of saturated sodium bicarbonate solution are added, while stirring vigorously. The stirring is continued for about 10 minutes with extraction, the organic phase is separated and dried over magnesium sulfate.

1 Gram of methylsulfonic acid is added, the mixture is stirred for 2 hours at room temperature, and the solid matter is filtered.

Decomposition starts at 118° C., the IR spectrum is identical with the compound prepared under (a) above.

EXAMPLE 99

3-Ethyl-2-N,N-diethyliminio-4-(4-chloro-3-sulfamoyl-phenyl)-1,3-thiazolidine-4-ol-chloride 4.74 Grams of 3-ethyl-2-N,N-diethyliminio-4-(4-chloro-3-sulfamoyl-phenyl)-1,3-thiazolidine-4-ol-bromide are introduced into 50 ml of $H_2O$, then about 100 ml of ethyl acetate are added to the mixture to form a layer, subsequently 10 ml of saturated sodium bicarbonate solution are added, and the whole is stirred vigorously for about 10 minutes.

The organic phase is separated, dried over magnesium sulfate, then an ethereal HCl solution is added until the reaction becomes strongly acid, and the crystalline suspension obtained is stirred for about 30 minutes.

Colorless crystals, melting point 170° to 172° C. (decomposition).

EXAMPLE 100

2-N-Benzyl-N-methyliminio-4-(4-chloro-3-sulfamoyl-phenyl)-3-methyl-1,3-thiazolidine-4-ol-chloride is obtained according to Example 99 from 2-N-benzyl-N-methyliminio-4-(4-chloro-3-sulfamoyl-phenyl)-3-methyl-1,3-thiazolidine-4-ol-bromide.

Melting point 141° to 142° C. (decomposition).

EXAMPLE 101

4-(4-Chloro-3-sulfamoyl-phenyl)-3-methyl-2-N,N-tetramethyleneiminio-1,3-thiazolidine-4-ol-chloride is obtained according to Example 99 from 4-(4-chloro-3-sulfamoyl-phenyl)-3-methyl-2-N,N-tetramethylene-iminio-1,3-thiazolidine-4-ol-bromide.

Melting point 201° to 204° C. (decomposition).

EXAMPLE 102

2-N,N-Di-n-butyliminio-4-(4-chloro-3-sulfamoyl-phenyl)-3-methyl-1,3-thiazolidine-4-ol-chloride is obtained according to Example 99 from 2-N,N-di-n-butyliminio-4-(4-chloro-3-sulfamoyl-phenyl)-3-methyl-1,3-thiazolidine-4-ol-bromide.

Melting point 179° to 180° C. (decomposition).

EXAMPLE 103

3-Ethyl-2-N,N-diethyliminio-4-(4-chloro-3-dimethyl-sulfamoylphenyl)-1,3-thiazolidine-4-ol-chloride 2.9 Grams of 4'-chloro-3'-dimethylsulfamoyl-acetophenone-2-thiol are added to 1.6 g of N,N',N'-triethyl-chloroformamidine in 20 ml of isopropanol, the mixture is stirred for 10 hours at room temperature and for another 2 hours at 35° C. After the addition of 30 ml of diethylether the mixture is stirred for 1 hour, the solvent is decanted off, and the viscous residue is brought to crystallization under ethyl acetate.

Colorless crystals, melting point 131° C.

EXAMPLE 104

4-(4-Chloro-3-sulfamoyl-phenyl)-3-cyclopropyl-2-N,N-dimethyliminio-1,3-thiazolidine-4-ol-bromide is obtained according to Example 6 from 2-bromo-4'-chloro-3'-sulfamoyl-acetophenone and 1-cyclopropyl-3,3-dimethyl-thio-urea. Amorphous solid matter, decomposition starting at 97° C.

The novel thio-ureas of the formula III used as starting compounds in the above Examples have been prepared according to methods which are known in literature [cf. Houben-Weyl, "Methoden der organischen Chemie", vol. 9, page 884, 4th edition (1955)].

The melting points of some compounds of the formula III have been specified in Table II below.

TABLE II:

| | Thio-ureas of the formula III | | | |
|---|---|---|---|---|
| $R^1$ | $R^2$ | $R^3$ | Melting Point | Remarks |
| $CH_3$ | $C_2H_5$ | n-$C_4H_9$ | — | oil |
| $CH_3$ | $CH(CH_3)_2$ | $CH(CH_3)_2$ | 79° C | — |
| $C_2H_5$ | —$(CH_2)_4$— | | 87° C | — |
| $C_2H_5$ | $CH_2=CH-CH_2$ | $CH_2=CH-CH_2$ | — | oil |
| $C_2H_5$ | $CH_2=CH-CH_2$ | —⟨C$_6$H$_5$⟩— (phenyl) | — | oil |
| $C_2H_5$ | n-$C_4H_9$ | $C_6H_5$ | 49° C | — |
| $CH_3$ | $CH_3-CH-(CH_2)_3-CH-CH_3$ | | 164° C | — |
| $CH_3$ | $CH_3-CH-(CH_2)_4-$ | | 69° C | — |
| $CH_3$ | $-CH_2-CH-O-CH-CH_2-$ with $CH_3$, $CH_3$ | | — | oil |
| $CH_2=CH-CH_2$ | —$(CH_2)_4$— | | 70° C | — |

TABLE II:-continued

| | Thio-ureas of the formula III | | Melting Point | Remarks |
|---|---|---|---|---|
| R¹ | R² | R³ | | |
|  | $C_2H_5$ | $C_2H_5$ | — | oil |
| $CH_3$ | | $-(CH_2)_6-$ | 96° C | — |
| $CH_3$ | $CH(CH_3)_2$ | $CH_2C_6H_5$ | 80° C | — |
| | $-(CH_2)_3-$ | $CH_3$ | 82° C | — |

We claim:

1. Thiazolidine of the formula

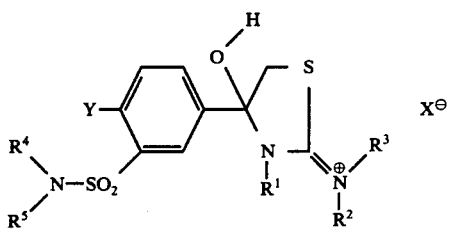

in which $R^1$ represents alkyl or alkenyl of up to 4 carbon atoms or cycloalkyl of 3 to 6 carbon atoms, $R^2$ and $R^3$ are identical or different and represent alkyl of 1 to 6 carbon atoms, cycloalkyl of 3 to 6 carbon atoms, alkenyl of 3 to 4 carbon atoms, phenylalkyl of 1 to 3 carbon atoms in the alkyl moiety, piperonyl or phenyl, Y represents hydrogen, bromine or chlorine, $R^4$ stands for hydrogen or an alkyl of 1 to 4 carbon atoms, $R^5$ is hydrogen, alkyl of 1 to 4 carbon atoms, cycloalkyl of 5 to 7 carbon atoms, benzyl, hexahydrobenzyl, chlorobenzyl, methylbenzyl or phenylethyl, and X represents the anion of a pharmacologically tolerated acid.

2. A compound as claimed in claim 1, which is 3-ethyl-4-(4-chloro-3-sulfamoyl-phenyl)-2-diethyliminio-1,3-thiazolidine-4-ol-chloride.

3. A compound as claimed in claim 1, which is 3-ethyl-4-(4-chloro-3-sulfamoyl-phenyl)-2-diethyliminio-1,3-thiazolidine-4-ol-bromide.

4. A compound as claimed in claim 1, which is 3-ethyl-4-(4-chloro-3-sulfamoyl-phenyl)-2-diallyliminio-1,3-thiazolidine-4-ol-chloride.

5. A compound as claimed in claim 1, which is 2-N-benzyl-N-methyliminio-4-(4-chloro-3-sulfamoyl-phenyl)-3-methyl-1,3-thiazolidine-4-ol-chloride.

6. A method of treatment which comprises administering to a patient in need of salidiuretic treatment an effective amount of a compound as defined in claim 1.

7. A pharmaceutical composition having salidiuretic activity and essentially containing a salidiuretically effective proportion of a compound as claimed in claim 1.

8. A pharmaceutical composition having salidiuretic activity and essentially containing 10 to 100 mg per dosage unit of a compound as defined in claim 6.

9. A method of treatment which comprises administering to a patient in need of salidiuretic treatment an effective amount of the compound defined in claim 2.

10. A pharmaceutical composition having salidiuretic activity and essentially containing a salidiuretically effective proportion of the compound defined in claim 2.

11. A pharmaceutical composition having salidiuretic activity and essentially containing 10 to 100mg per dosage unit of the compound defined in claim 2.

* * * * *